(12) United States Patent
Ouchi

(10) Patent No.: US 6,402,686 B1
(45) Date of Patent: Jun. 11, 2002

(54) FULLY-SWALLOWABLE ENDOSCOPIC SYSTEM

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 152 days.

(21) Appl. No.: 09/588,307

(22) Filed: Jun. 6, 2000

(30) Foreign Application Priority Data

Jun. 7, 1999 (JP) ............................................ 11-160029

(51) Int. Cl.⁷ .............................................. A61B 1/307
(52) U.S. Cl. ...................... 600/139; 600/109; 600/130; 600/141; 600/151
(58) Field of Search ................................ 600/101, 109, 600/128, 130, 136, 139, 143, 151, 152, 141; 348/65, 68, 71, 74

(56) References Cited

U.S. PATENT DOCUMENTS

| 4,633,304 A | * 12/1986 | Nagasaki ..................... 128/903 |
| 5,398,670 A | * 3/1995 | Ortiz et al. .................. 385/119 |
| 5,595,565 A | * 1/1997 | Treat et al. .................. 600/101 |
| 5,604,531 A | * 2/1997 | Iddan et al. ................... 348/76 |
| 5,662,587 A | * 9/1997 | Grundfest et al. .......... 600/114 |
| 6,162,171 A | * 12/2000 | Ng et al. ..................... 600/101 |
| 6,240,312 B1 | * 5/2001 | Alfano et al. ............... 128/903 |

FOREIGN PATENT DOCUMENTS

| JP | 64-4450 | 1/1989 |
| JP | 64-76822 | 3/1989 |
| JP | 3-9705 | 1/1991 |
| JP | 4-144533 | 5/1992 |
| JP | 6-114064 | 4/1994 |
| JP | 7-111985 | 5/1995 |

\* cited by examiner

*Primary Examiner*—John P. Leubecker
(74) *Attorney, Agent, or Firm*—Greenblum & Bernstein, P.L.C.

(57) ABSTRACT

A fully-swallowable endoscopic system includes a rod-shaped endoscope body which can be swallowed entirely by a patient to be examined so as to be placed in a body cavity, the rod-shaped endoscope body including two bendable portions having different lengths which are respectively provided close to the opposite ends of the rod-shaped endoscope body; and an external device provided separately from the rod-shaped endoscope body having no mechanical connection with the rod-shaped endoscope body. The rod-shaped endoscope body is provided therein with at least one light emitter, at least one observing system, a transmitter for transmitting a radio wave which carries an image formed by the observing system, and a power supplying device. The external device includes a receiver for receiving the radio wave which carries the image.

13 Claims, 10 Drawing Sheets

FULLY-SWALLOWABLE ENDOSCOPIC SYSTEM

BACKGROUND OF THE INVENTION

1. Field of the Invention

The present invention relates to a fully-swallowable endoscopic system which can be retained in the patient's body for a long time, wherein few blind spots occur in an endoscopy examination.

2. Description of the Related Art

In an endoscopy examination, in general, an insertion portion connected to an operation portion is introduced into a patient's body through his or her mouth to observe a target inner part of the body. In the case of observing an inner part of a largely-bent tubular passage in a body such as part of the large intestine, the occurrence of blind spots in the endoscopy examination cannot be avoided.

The body insertion portion of the endoscope must be sometimes inserted and retained in the body for a long time to observe the progress of a diseased part within the body or obtain and/or record somatoscopic information of a patient under ordinary every-day living conditions. However, the insertion and retainment of the endoscope in the body through the patient's mouth causes the patient to suffer from significant pain.

To relieve pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member the night before the day of examination, so that the soft ball is discharged from the patient's anus the next day. An operator pulls or moves the tip end and the tail end of the flexible continuous member to thereby move or guide the capsule connected to the intermediate portion of the flexible continuous member.

In the capsule type of endoscope described above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is generally difficult to control the position of the endoscope when in the form of a capsule.

SUMMARY OF THE INVENTION

It is an object of the present invention to provide a fully-swallowable endoscopic system which can relieve a patient to be examined from pain and which makes it possible to observe the target inner part of the body surely and precisely.

To achieve the object mentioned above, according to the present invention, a fully-swallowable endoscopic system is provided, which includes a rod-shaped endoscope body which can be swallowed entirely by a patient to be examined so as to be placed in a body cavity, the rod-shaped endoscope body including two bendable portions having different lengths which are respectively provided close to the opposite ends of the rod-shaped endoscope body, each of the two bendable portions being bendable along a curve of the body cavity; and an external device provided separately from the rod-shaped endoscope body having no mechanical connection with the rod-shaped endoscope body. The rod-shaped endoscope body is provided therein with at least one light emitter, at least one observing system, a transmitter for transmitting a radio wave which carries an image formed by the observing system, and a power supplying device. The external device includes a receiver for receiving the radio wave which carries the image.

Preferably, the rod-shaped endoscope body includes a flexible portion which bends when an external force is applied thereto, the flexible portion being positioned between the two bendable portions to connect the two bendable portions, and wherein each of the two bendable portions includes a bending portion which can be radio-controlled to bend by an operation of the external device. The rod-shaped endoscope body is provided therein with a radio-controlled driving device which receives a radio operational signal transmitted from the external device to bend the bending portion in accordance with the radio operational signal, and the external device includes an operational portion which is operated to transmit the radio operational signal to the radio-controlled driving device.

In an embodiment, the rod-shaped endoscope body includes more than one light emitter and more than one observing system which are positioned at different locations.

Preferably, the radio-controlled driving device includes a plurality of drive wires made of a shape memory alloy, and a selective-heating device which selectively heats the plurality of drive wires to bend the bending portion.

The power supplying device can be a built-in battery.

In an embodiment, the external device includes a microwave transmitter for transmitting a microwave to the rod-shaped endoscope body, wherein the power supplying device converts the microwave into electrical current to supply the electrical current to the rod-shaped endoscope body.

Preferably, the observing system includes an objective optical system and a CCD image sensor.

Preferably, the external device includes a monitor which visually indicates the image.

According to another aspect of the present invention, a fully-swallowable endoscopic system is provided, which includes a rod-shaped endoscope body having a first bending portion, a flexible portion and a second bending portion which are arranged in that order, one of the first and second bending portions being longer than the other; and a radio controller for manipulating each of the first and second bending portions so as to bend by radio-control. The rod-shaped endoscope body is provided therein with at least one light emitter for illuminating a target inner part of a living body, at least one image pick-up device for taking an image of the target inner part illuminated by the at least one light emitter, and a transmitter for transmitting a radio wave which carries the image taken by the image pick-up device.

In an embodiment, the rod-shaped endoscope body further includes a first hard portion fixed to one of the opposite ends of the rod-shaped endoscope body, and one of the at least one light emitter and one of the at least one image pick-up device are fixed to the first hard portion.

Preferably, the rod-shaped endoscope body further includes a second hard portion fixed to the other of the opposite ends of the rod-shaped endoscope body, and another of the at least one light emitter and another of the at least one image pick-up device are fixed to the second hard portion.

Preferably, the radio controller includes a monitor and a receiver for receiving the radio wave to indicate the image on the monitor.

In an embodiment, the radio controller further includes a second transmitter for transmitting a microwave to the rod-shaped endoscope body, and wherein the rod-shaped endoscope body is provided therein with a power supplying device which receives the microwave to convert the microwave into electrical current which is to be used as a power source of the rod-shaped endoscope body.

The present disclosure relates to subject matter contained in Japanese Patent Application No.11-160029 (filed on Jun. 7, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENTS

Figure 1:
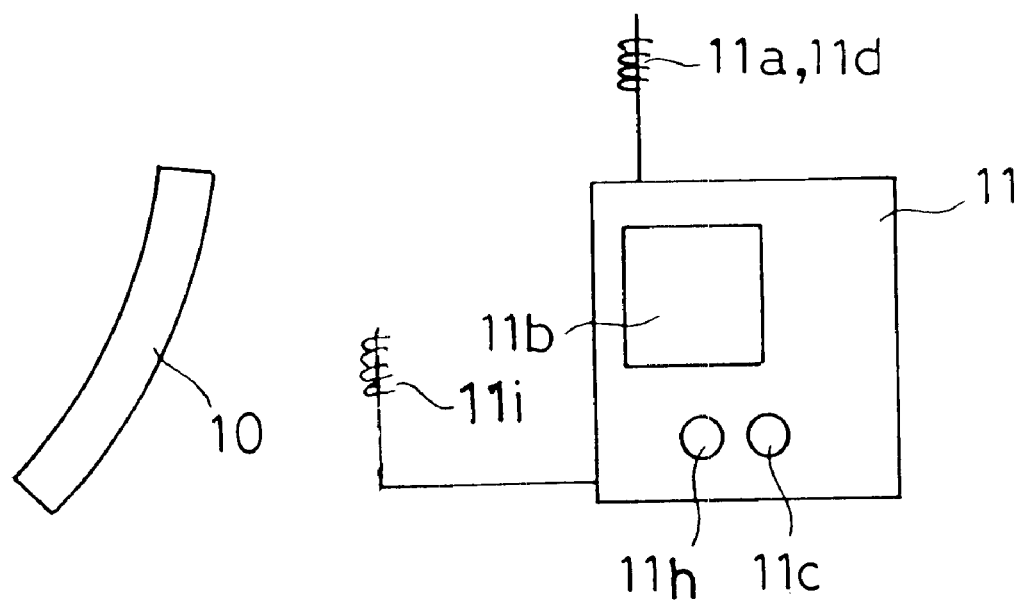
FIG. 1 is a schematic view of an embodiment of a fully-swallowable endoscopic system having a rod-shaped endoscope body and an external device, according to the present invention.
Figure 2:
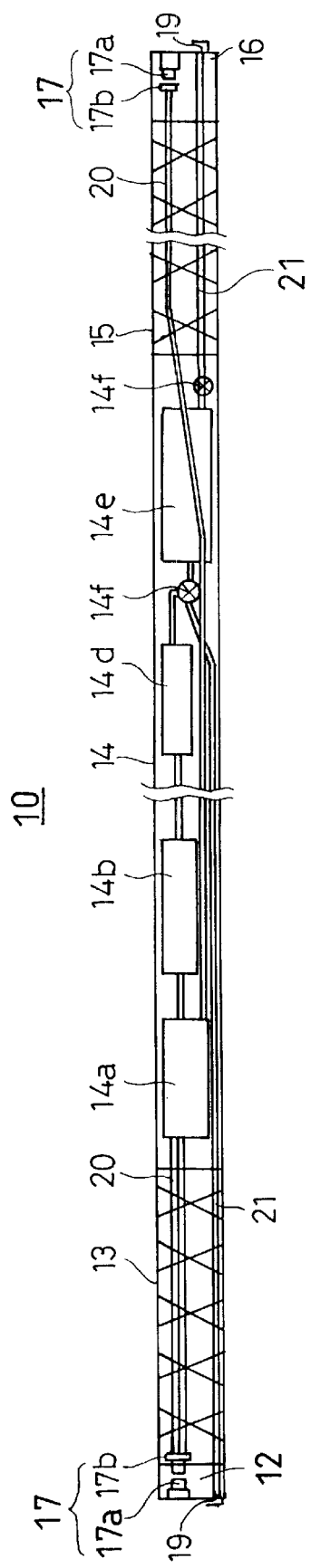
FIG. 2 is a schematic cross sectional view of the first embodiment of the rod-shaped endoscope body, according to the present invention.

FIG. 1 shows an embodiment of a fully-swallowable endoscopic system which includes a rod-shaped endoscope body 10 and an external device 11. A patient to be examined swallows the rod-shaped endoscope body 10 before an endoscopic examination is performed with the endoscope 10. The external device 11 functions as a wireless controller (radio controller) and a power supply for the endoscope 10.

FIGS. 2 through 5 show the first embodiment of the rod-shaped endoscope body 10. The rod-shaped endoscope body 10 is provided with a first hard portion (unbendable portion) 12, a first bending portion 13, a flexible portion 14, a second bending portion 15 and a second hard portion (unbendable portion) 16, in this order from the front end (the left end as viewed in FIG. 2). The first bending portion 13 and the flexible portion 14 constitute a bendable portion, and the second bending portion 15 and the flexible portion 14 constitute another bendable portion. The rod-shaped endoscope body 10 is entirely covered by an elastic covering 28 whose outer surface is smooth and well-slidable (see FIG. 12). The first and second hard portions 12 and 16 are each made of a hard material (e.g., a hard plastic) which is not macroscopically deformable. The flexible portion 14 is designed to be bendable along the shape of a digestive tract when it is inserted in a body cavity.

Figure 3:
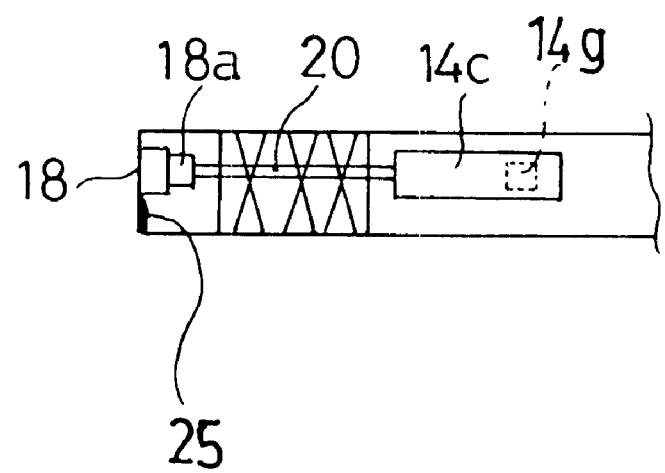
FIG. 3 is a schematic cross sectional view of part of the rod-shaped endoscope body shown in FIG. 2, taken along a different plane.

Each of the hard portions 12 and 16 is provided therein with an observing system 17, an illumination window 18 and an air supply port 19. Each observing system 17 includes an objective optical system 17a and a CCD image sensor 17b. The flexible portion 14 is provided therein with an amplifier circuit 14a, a transmitter/receiver device 14b, a power supplying device 14c, a control circuit 14d, a compressed air tank 14e and a microwave receiver 14g as shown in FIG. 3. Each CCD image sensor 17b is connected to the amplifier circuit 14a via a corresponding signal line 20. The amplifier circuit 14a is connected to the transmitter/receiver device 14b, which is positioned in the flexible portion 14. Each of the hard portions 12 and 16 is provided therein with an LED (light emitter) 18a which is secured to the corresponding illumination window 18. Each ED 18a is connected to the control circuit 14d via a corresponding signal line 20 (see FIG. 3).

Each air supply port 19 is connected to the outer end of a corresponding air supply tube 21. The inner end of each air supply tube 21 is connected to a corresponding valve 14f of the compressed air tank 14e. Each valve 14f is controlled to open or shut by the control circuit 14d. The power supplying device 14c is connected to the transmitter/receiver device 14b and the control circuit 14d. The power supplying device 14c converts a microwave received by the microwave receiver 14g into electrical current to supply the same to the transmitter/receiver device 14b and the control circuit 14d. The microwave received by the microwave receiver 14g is transmitted from the external device 11.

Figure 12:
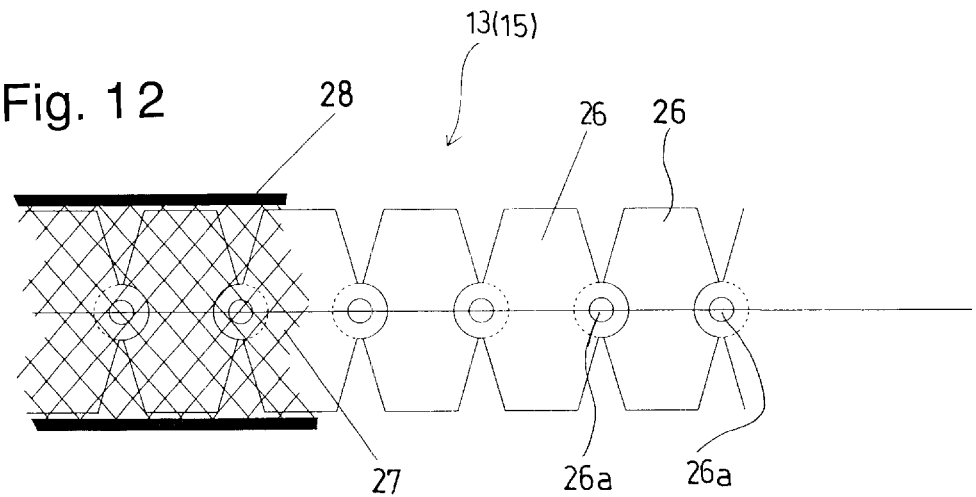
FIG. 12 is a schematic side view of part of the first embodiment of the bending portion, with parts omitted for clarity, in the case where the bending portion is designed to be bendable in a single plane.

FIG. 12 shows part of the first embodiment of each of the first and second bending portions 13 and 15 in the case where each bending portion is designed to be bendable in a single plane. The first embodiment of each bending portion is provided with an articulated series of ring joints 26. Adjacent ring joints 26 are connected with each other by a shaft 26a so that each of the adjacent ring joints 26 can rotate about the shaft 26a. All the shafts 26a are parallel to one another so as to lie in a common plane. The articulated series of ring joints 26 having such a structure is covered by a steel wired tube 27. This steel wired tube 27 is covered by the aforementioned elastic covering 28. Each of the first and second bending portions 13 and 15 is designed to be more flexible and bendable than the flexible portion 14 to bend from the flexible portion 14. Namely, each of the opposite ends of the rod-shaped endoscope body 10 is designed as a bendable portion. The length of the second bending portion 15 is greater than that of the first bending portion 13 (see FIGS. 4 and 5).

Figure 4:
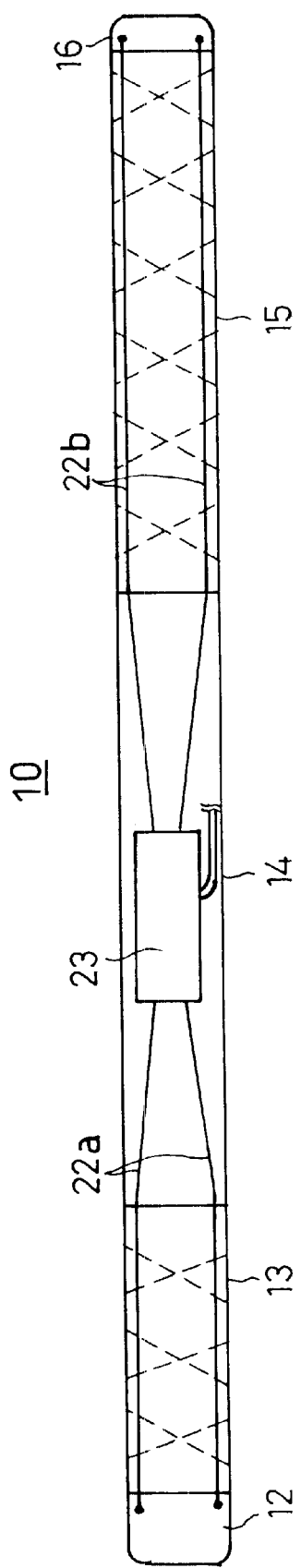
FIG. 4 is a schematic cross sectional view of the rod-shaped endoscope body shown in FIG. 2, showing a radio-controlled bending device thereof.
Figure 5:
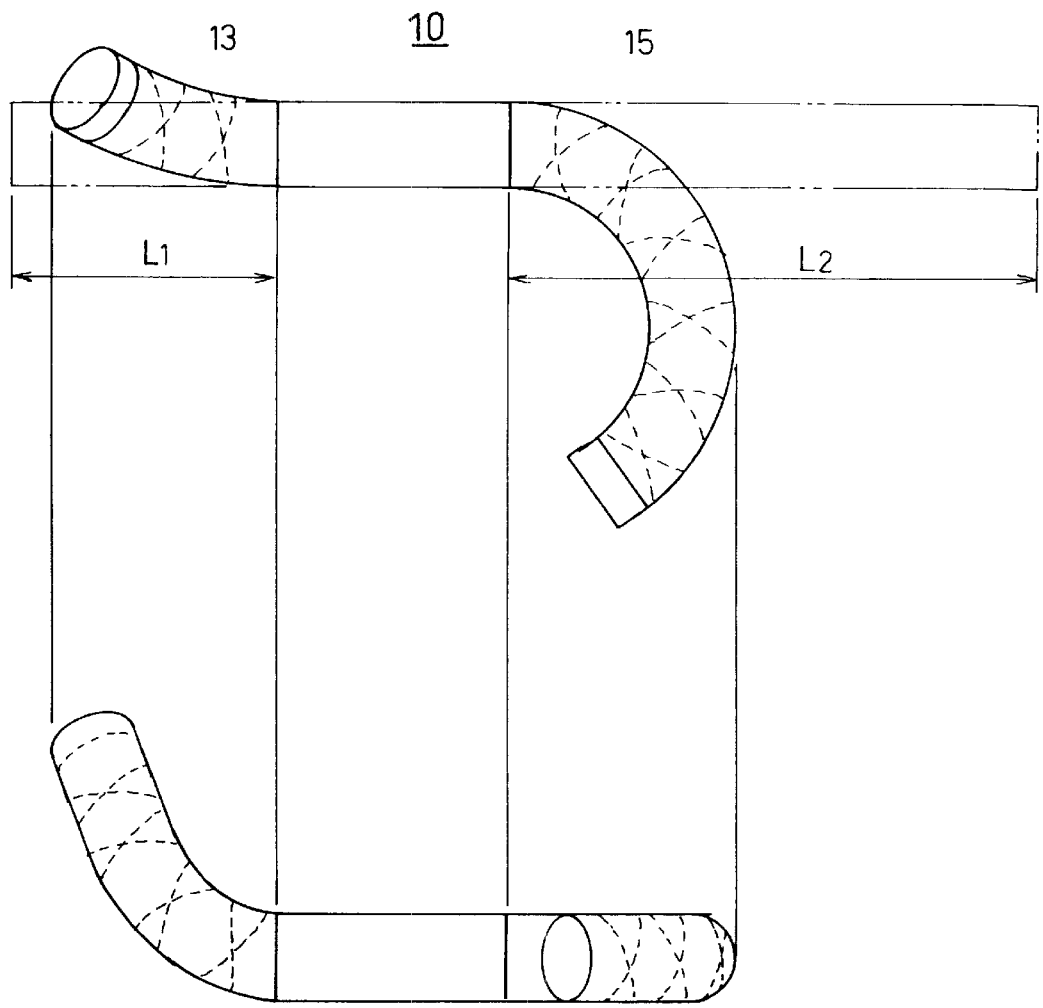
FIG. 5 is an explanatory view of the rod-shaped endoscope body shown in FIG. 2, showing the difference in length between the first and second bending portions.

The rod-shaped endoscope body 10 is provided therein with a plurality of bendable drive wires (two drive wires in the first embodiment of the first bending portion 13) 22a which extend within the first bending portion 13 and the flexible portion 14 (see FIG. 4). Each drive wire 22a is made of a shape memory alloy (SMA) which bends when supplied with electrical current to be heated thereby. The rod-shaped endoscope body 10 is further provided therein with a selective-heating device 23 which is connected to the transmitter/receiver device 14b. The drive wires 22a, the selective heating device 23, and the transmitting/receiving device 14b constitute a radio-controlled driving device. The outer ends of the drive wires 22a are each secured to the first hard portion 12, while the inner ends of the drive wires 22a are each secured to the selective-heating device 23.

The two drive wires 22a are diametrically arranged at opposite sides of the axis of the cylindrical first bending portion 13. The selective-heating device 23 is a circuit which selectively supplies electrical current to the two drive wires 22a to heat the same in accordance with control signals output from the transmitter/receiver device 14b, which makes it possible to bend the first bending portion 13 in a plane in which the two drive wires 22a lie.

Figure 11:
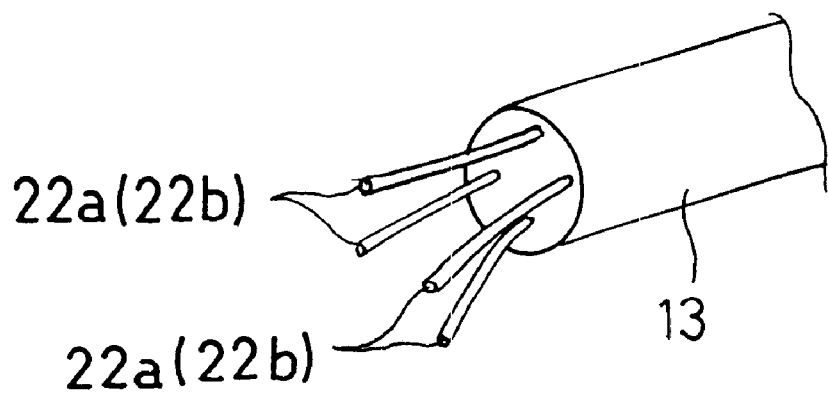
FIG. 11 is an explanatory view of part of the second embodiment of the bending portion of the rod-shaped endoscope body, showing an arrangement of the bendable drive wires provided in the bending portion.
Figure 13:
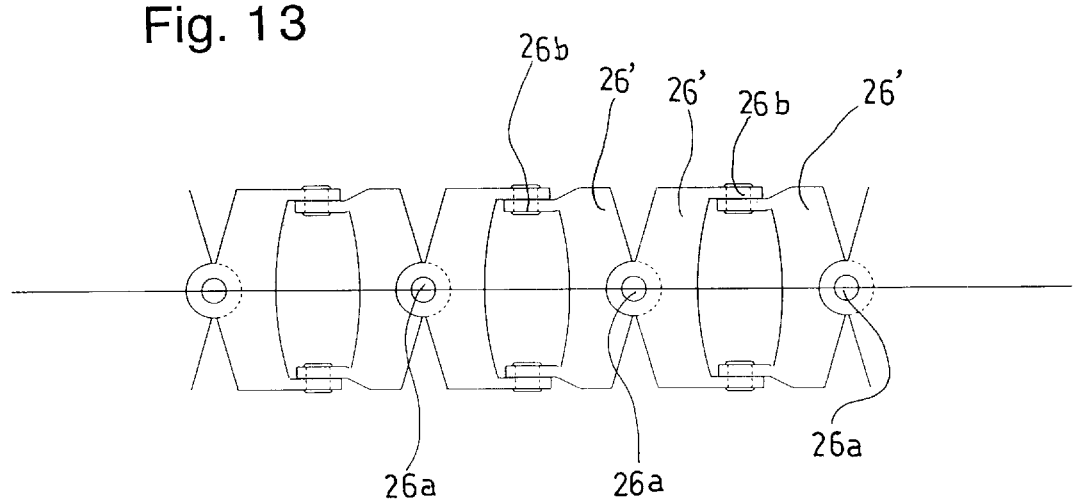
FIG. 13 is a schematic side view of part of the second embodiment of the bending portion, in the case where the bending portion is designed to be bendable in two planes perpendicular to each other.

When it is required that the first bending portion 13 be bendable only in a single plane, it is sufficient that the rod-shaped endoscope body 10 be provided with the first embodiment of the first bending portion 13, as shown in FIG. 12, which can bend only in a single plane. When it is required that the first bending portion 13 be bendable in two planes perpendicular to each other, the first bending portion 13 needs to have a structure such as shown in FIG. 13. FIG. 13 shows part of the second embodiment of each of the first and second bending portions 13 and 15 in the case where it is designed to be bendable in two planes perpendicular to each other. The second embodiment of each bending portion is provided with an articulated series of ring joints 26'. Adjacent ring joints 26' are connected with each other by a first shaft 26a or a second shaft 26b so that each of the adjacent ring joints 26' can rotate about each of the shafts 26a and 26b. The first and second shafts 26a and 26b extend in directions perpendicular to each other and are alternately arranged. In FIG. 13, neither the steel wired tube 27 nor the aforementioned elastic covering 28 is illustrated for clarity of illustration. In the second embodiment of the first bending portion 13, four bendable drive wires 22a extend within the first bending portion 13 and the flexible portion 14 (see FIG. 11). The outer ends of the four drive wires 22a are each secured to the first hard portion 12 at 90 intervals about the axis of the first hard portion 12. The inner ends of each pair of drive wires 22a which are diametrically opposite to each other are secured to the selective-heating device 23. In the second embodiment of the first bending portion 13, although only two drive wires 22a are shown in FIG. 4, the remaining two drive wires 22a are provided in a similar manner.

Similar to the first bending portion 13, the rod-shaped endoscope body 10 is provided therein with another plurality of bendable drive wires (two drive wires in the first embodiment of the second bending portion 15) 22b which extend within the second bending portion 15 and the flexible portion 14 (see FIG. 4). Each drive wire 22b is made of a shape memory alloy (SMA) which bends when supplied with electrical current to be heated thereby. The outer ends of the drive wires 22b are each secured to the selective-heating device 23, while the inner ends of the same are each secured to the second hard portion 16.

The two drive wires 22b are diametrically arranged at opposite sides of the axis of the cylindrical second bending portion 15. The selective-heating device 23 is a circuit which selectively supplies electrical current to the two drive wires 22b to heat the same in accordance with control signals output from the transmitter/receiver device 14b, which makes it possible to bend the second bending portion 15 in a plane in which the two drive wires 22b lie.

When it is required that the second bending portion 15 be bendable only in a single plane, it is sufficient that the rod-shaped endoscope body 10 be provided with the first embodiment of the second bending portion 15, as shown in FIG. 12, which can bend only in a single plane. When it is required that the second bending portion 15 be bendable in two planes perpendicular to each other, the second bending portion 15 needs to have a structure such as shown in FIG. 13, similar to the second embodiment of the first bending portion 13. In the second embodiment of the second bending portion 15, similar to the second embodiment of the first bending portion 13, four bendable drive wires 22b extend within the second bending portion 15 and the flexible portion 14 (see FIG. 11). The outer ends of the four drive wires 22b are each secured to the second hard portion 16. The inner ends of each pair of drive wires 22b which are diametrically opposite to each other are secured to the selective-heating device 23. In the second embodiment of the second bending portion 15, although only two drive wires 22b are shown in FIG. 4, the remaining two drive wires 22b are provided in a similar manner.

Figure 10:
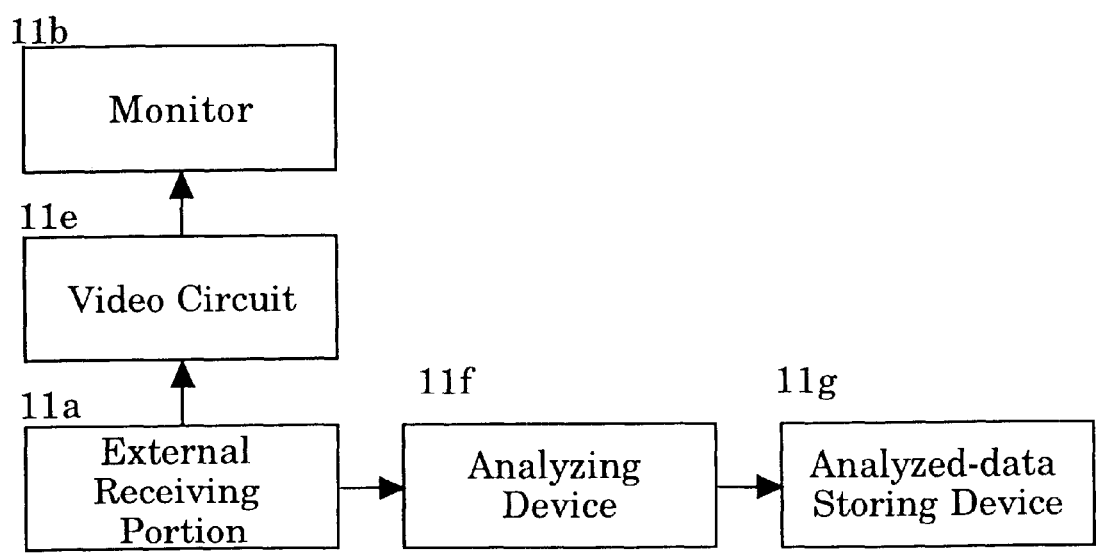
FIG. 10 is a block diagram of a process which is performed after the external device receives a signal output from the rod-shaped endoscope body.

The external device 11 shown in FIG. 1 is provided with an external receiving portion 11a, a monitor 11b, a bending portion controller portion (operational portion) 11c, an external transmitting portion 11d, a valve controlling portion 11h and a microwave transmitting portion (microwave transmitter) 11i. The external device 11 is further provided with a video circuit 11e, an analyzing device 11f and an analyzed-data storing device 11g (see FIG. 10). The external device 11 transmits the aforementioned microwave, which is used as a power supply for the rod-shaped endoscope body 10, from the microwave transmitting portion 11i to the rod-shaped endoscope body 10. This transmitted microwave is received by the microwave receiver 14g and is converted into electrical current by the power supplying device 14c. The power supplying device 14c supplies the electrical current to the transmitter/receiver device 14b and the control circuit 14d. By manually operating the bending portion controller portion 11c and the valve controlling portion 11h of the external device 11, radio operational signals for operating the first or second bending portion 13 or 15 and the valve 14f are generated by the external device 11 to be transmitted to the rod-shaped endoscope body 10 via the external transmitting portion 11d. The external receiving portion 11a receives image signals (radio waves) transmitted from the transmitter/receiver device 14b. The received image signals are displayed on the monitor 11b to be observed by an operator.

Figure 6:
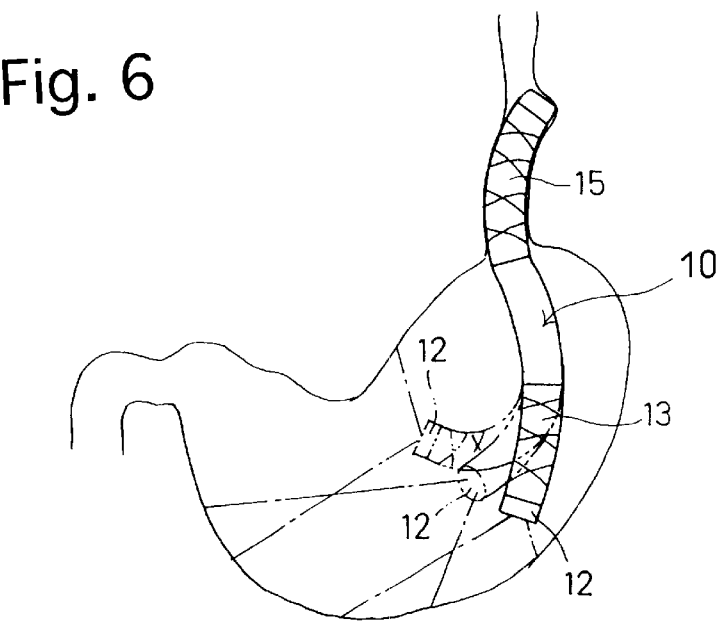
FIG. 6 is an explanatory view of the rod-shaped endoscope body which is positioned between the esophagus and the stomach, showing a state where the inside of the stomach is observed with the front observing system while making the posture of the endoscope stable by the rear bending portion of the endoscope.
Figure 7:
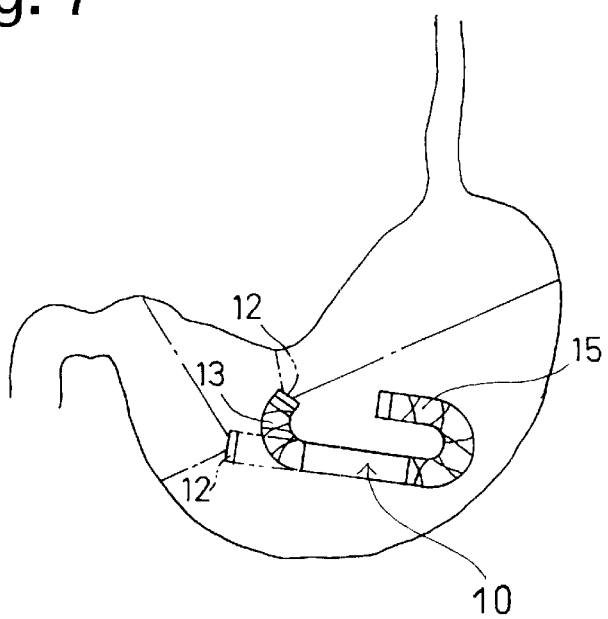
FIG. 7 is an explanatory view of the rod-shaped endoscope body which is positioned in the stomach, showing a state where the inside of the stomach is observed with the front observing system while making the posture of the endoscope stable by the rear bending portion of the endoscope.
Figure 8:
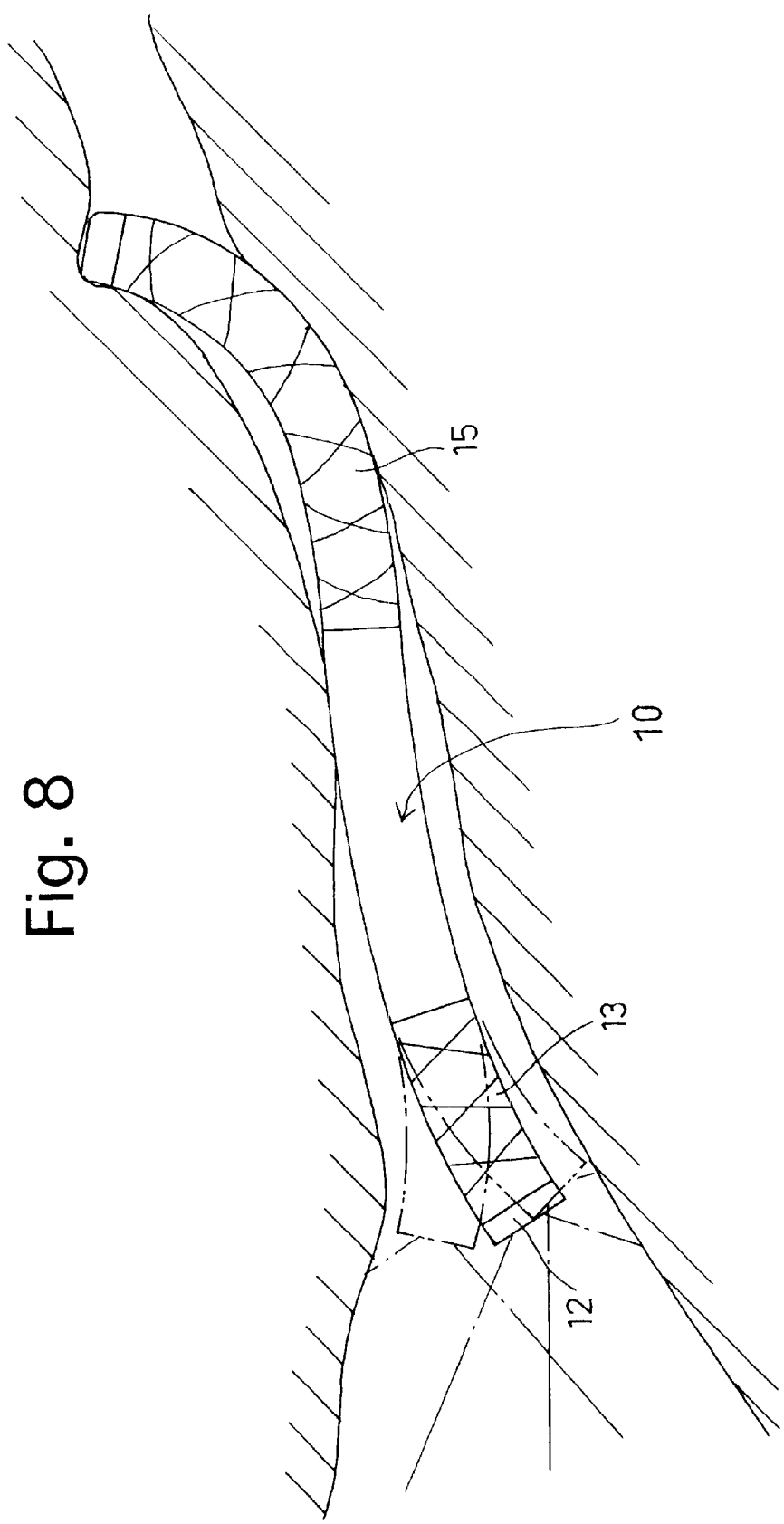
FIG. 8 is an explanatory view of the rod-shaped endoscope body which is positioned in a tubular passage in a body, showing a state where the inside thereof is observed with the front observing system with the rear bending portion being fixed to an inner wall of the tubular passage by bending the rear bending portion.

In the fully-swallowable endoscope constructed as above, a patient to be examined swallows the rod-shaped endoscope body 10 entirely from the front end thereof, i.e., from the first hard portion 12. After being swallowed entirely, the rod-shaped endoscope body 10 is radio-controll ed to proceed gradually along the alimentary canal by peristalsis. When the first hard portion 12 reaches the stomach as shown in FIG. 6, the second bending portion 15, which is positioned at the rear end of the rod-shaped endoscope body 10, can be fixed to an inner wall of the esophagus by bending the second bending portion 15. This makes it easy to observe the inside of the stomach with the rod-shaped endoscope body 10. In the case where the endoscope 10 is in a narrow tubular passage in a body, the endoscope 10 can be stably held thereinside by pressing the second bending portion 15 against an inner wall of the canal by bending the second bending portion 15 so that the inside of the canal can be widely observed by manipulating the first bending portion 13. Since the second bending portion 15 is designed to be longer than the first bending portion 13 so as to bend largely, the target inner part of the body can be observed with the observing system 17 in the first hard portion 12 by manipulating the first bending portion 13 while the endoscope 10 is stably held by the widely-bent second bending portion 15 (see FIG. 7).

In the present embodiment of the fully-swallowable endoscopic system, the transmitter/receiver device 14b of the rod-shaped endoscope body 10 receives the radio operational signals transmitted from the external transmitting portion 11d of the external device 11 so that each of the fundamental operational elements of the rod-shaped endoscope body 10 can be radio-controlled by operating the external device 11. The power supplying device 14c supplies electrical current to the transmitter /receiver device 14b and the control circuit 14d by converting the received microwave into electrical current, so that the operator does not have to care about the remaining battery power of the rod-shaped endoscope body 10.

This makes it possible to observe the target inner part of the body sufficiently.

Each LED 18a, which receives power from the power supplying device 14c via the corresponding signal line 20, emits light outwardly through the corresponding illumination window 18. The object image upon which the illumination light of each LED 18a is impinged is formed on the sensitive surface of the corresponding CCD image sensor 17b through the corresponding objective optical system 17a. The image signal supplied from each CCD image sensor 17b is amplified by the amplifier circuit 14a. This amplified image signal is transmitted from the transmitter/receiver device 14b to be subsequently received by the external receiving portion 11a of the external device 11. The image signal received by the external device 11 is processed by the video circuit 11e to be observed on the monitor 11b (see FIG. 10). The operator operates the bending portion controller portion 11c of the external device 11 to bend the first bending portion 13 or the second bending portion 15 via the selective-heating device 23, which is controlled by the radio operational signals transmitted from the external transmitting portion 11d, to thereby change the direction of the objective optical system 17a to observe the target inner part of the body. At this time, if a tubular passage in a body is made to inflate by sending the compressed air in compressed air tank 14e from the corresponding air supply port 19 to the tubular passage via the corresponding air supply tube 21 by operating the valve controlling portion 11h of the external device 11, so that the transmitter /receiver device 14b receives radio operational signals transmitted from the external transmitting portion 11d, so as to operate the corresponding valve 14f, the distance between the first or second hard portion 12 or 16 and the inner wall of the tubular passage becomes large, which makes it easy to observe the inner wall of the tubular passage.

A measuring device 25 for measuring information about a living body such as pH value, temperature, the amount of oxygen contained in blood, the hardness of the surface of cells, and the like, can be incorporated in the rod-shaped endoscope body 10 (see FIG. 3). In this case, the measured information can be transmitted from the transmitter/receiver device 14b to be received by the external receiving portion 11a of the external device 11. The received information can be analyzed and stored if the analyzing device 11f analyzes the received information while the analyzed-data storing device 11g stores the analyzed information (see FIG. 10).

Figure 9:
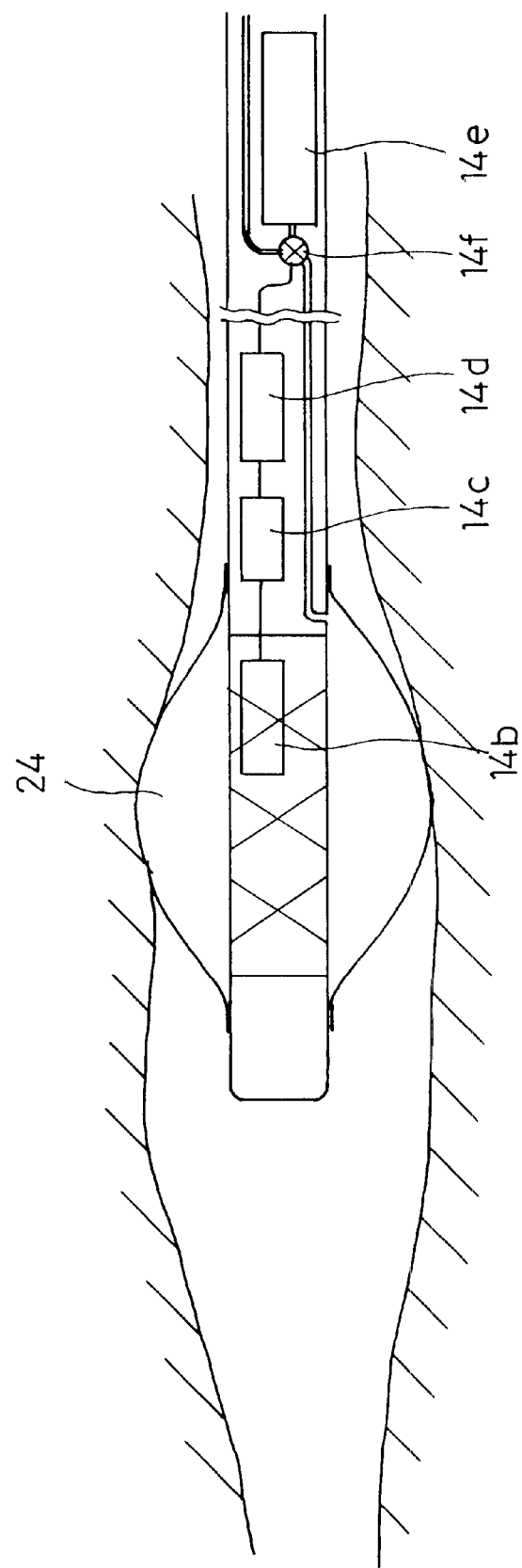
FIG. 9 is a schematic cross sectional view of fundamental components of the second embodiment of the rod-shaped endoscope body, positioned in a tubular passage in a body, according to the present invention.

FIG. 9 shows the second embodiment of the rod-shaped endoscope body 10. This rod-shaped endoscope body 10 is provided with a balloon 24 provided at one end (the front end in this particular embodiment shown in FIG. 9) of the rod-shaped endoscope body 10. The rod-shaped endoscope body 10 can be provided with two balloons respectively provided at the opposite ends of the rod-shaped endoscope body 10. The balloon 24 can be inflated by sending the compressed air in the compressed air tank 14e into the balloon 24, by operating the valve controlling portion 11h of the external device 11, so that the transmitter/receiver device 14b receives radio operational signals transmitted from the external transmitting portion 11d, so as to operate the valve 14f. For instance, in the case where the second embodiment of the rod-shaped endoscope body 10 is in a tubular passage in a body, if the balloon 24 is inflated, the distance between the hard portion 12 and the inner wall of the tubular passage becomes large, which makes it easy to observe the inner wall of the tubular passage.

The power supplying device 14c of the rod-shaped endoscope body 10 can be replaced by a built-in battery to simplify the structure of endoscopic system.

As can be understood from the foregoing, according to the fully-swallowable endoscopic system of the present invention, since the rod-shaped endoscope body is entirely positioned in a body cavity without any cables or wires which connect the rod-shaped endoscope body with the external device, a patient to be examined does not suffer from pain even if the endoscope is retained in the patient's body for a long time. Furthermore, since the bending portion provided at one end of the endoscope is designed to be longer or shorter than the bending portion provided at the other end of the endoscope, it is easy to stably hold the endoscope at a desired position.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A fully-swallowable endoscopic system comprising:
   a rod-shaped endoscope body which can be swallowed entirely by a patient to be examined so as to be placed in a body cavity, said rod-shaped endoscope body including two bendable portions having different lengths which are respectively provided close to the opposite ends of said rod-shaped endoscope body, each of said two bendable portions being bendable along a curve of said body cavity; and an external device provided separately from said rod-shaped endoscope body having no mechanical connection with said rod-shaped endoscope body;

wherein said rod-shaped endoscope body is provided therein with at least one light emitter; at least one observing system; a transmitter for transmitting a radio wave which carries an image formed by said observing system; and a power supplying device, and wherein said external device comprises a receiver for receiving said radio wave which carries said image.

2. The fully-swallowable endoscopic system according to claim 1, wherein said rod-shaped endoscope body comprises a flexible portion which bends when an external force is applied thereto, said flexible portion being positioned between said two bendable portions to connect said two bendable portions, and wherein each of said two bendable portions includes a bending portion which can be radio-controlled to bend by an operation of said external device, wherein said rod-shaped endoscope body is provided therein with a radio-controlled driving device which receives a radio operational signal transmitted from said external device to bend said bending portion in accordance with said radio operational signal, and wherein said external device includes an operational portion which is operated to transmit said radio operational signal to said radio-controlled driving device.

3. The fully-swallowable endoscopic system according to claim 1, wherein said rod-shaped endoscope body comprises more than one light emitter and more than one observing system which are positioned at different locations.

4. The fully-swallowable endoscopic system according to claim 2, wherein said radio-controlled driving device comprises a plurality of drive wires made of a shape memory alloy, and a selective-heating device which selectively heats said plurality of drive wires to bend said bending portion.

5. The fully-swallowable endoscopic system according to claim 1, wherein said power supplying device comprises a built-in battery.

6. The fully-swallowable endoscopic system according to claim 1, wherein said external device comprises a microwave transmitter for transmitting a microwave to said rod-shaped endoscope body, and wherein said power supplying device converts said microwave into electrical current to supply said electrical current to said rod-shaped endoscope body.

7. The fully-swallowable endoscopic system according to claim 1, wherein said observing system comprises an objective optical system and a CCD image sensor.

8. The fully-swallowable endoscopic system according to claim 1, wherein said external device comprises a monitor which visually indicates said image.

9. A fully-swallowable endoscopic system comprising:

a rod-shaped endoscope body which comprises a first bending portion, a flexible portion and a second bending portion which are arranged in that order, one of said first and second bending portions being longer than the other; and a radio controller for manipulating each of said first and second bending portions so as to bend by radio-control;

wherein said rod-shaped endoscope body is provided therein with at least one light emitter for illuminating a target inner part of a living body; at least one image pick-up device for taking an image of said target inner part illuminated by said at least one light emitter; and a transmitter for transmitting a radio wave which carries said image taken by said image pick-up device.

10. The fully-swallowable endoscopic system according to claim 9, wherein said rod-shaped endoscope body further comprises a first hard portion fixed to one of the opposite ends of said rod-shaped endoscope body, and wherein said one of said at least one light emitter and one of said at least one image pick-up device are fixed to said first hard portion.

11. The fully-swallowable endoscopic system according to claim 10, wherein said rod-shaped endoscope body further comprises a second hard portion fixed to the other of said opposite ends of said rod-shaped endoscope body, and wherein another of said at least one light emitter and another of said at least one image pick-up device are fixed to said second hard portion.

12. The fully-swallowable endoscopic system according to claim 9, wherein said radio controller comprises a monitor and a receiver for receiving said radio wave to indicate said image on said monitor.

13. The fully-swallowable endoscopic system according to claim 9, wherein said radio controller further comprises a second transmitter for transmitting a microwave to said rod-shaped endoscope body, and wherein said rod-shaped endoscope body is provided therein with a power supplying device which receives said microwave to convert said microwave into electrical current which is to be used as a power source of said rod-shaped endoscope body.

* * * * *